United States Patent
Wang et al.

(10) Patent No.: US 10,398,319 B2
(45) Date of Patent: Sep. 3, 2019

(54) ADVERSE PHYSIOLOGICAL EVENTS DETECTION

(71) Applicant: Huami Inc., Mountain View, CA (US)

(72) Inventors: Yuchen Wang, Mountain View, CA (US); Yuanxiang Wang, Mountain View, CA (US); Fei Wang, Mountain View, CA (US)

(73) Assignee: Huami Inc., Mountain View, CA (US)

( * ) Notice: Subject to any disclaimer, the term of this patent is extended or adjusted under 35 U.S.C. 154(b) by 168 days.

(21) Appl. No.: 15/359,048

(22) Filed: Nov. 22, 2016

(65) Prior Publication Data

US 2018/0140203 A1     May 24, 2018

(51) Int. Cl.
| | |
|---|---|
| *A61B 5/0205* | (2006.01) |
| *A61B 5/0404* | (2006.01) |
| *A61B 5/0476* | (2006.01) |
| *A61B 5/11* | (2006.01) |

(Continued)

(52) U.S. Cl.
CPC .......... *A61B 5/0205* (2013.01); *A61B 5/0006* (2013.01); *A61B 5/0404* (2013.01); *A61B 5/04017* (2013.01); *A61B 5/0476* (2013.01); *A61B 5/11* (2013.01); *A61B 5/681* (2013.01);

(Continued)

(58) Field of Classification Search
CPC . A61B 5/0205; A61B 5/0006; A61B 5/04017; A61B 5/0404; A61B 5/0476; A61B 5/11; A61B 5/681; A61B 5/721; A61B 5/7267; A61B 2562/0219
See application file for complete search history.

(56) References Cited

U.S. PATENT DOCUMENTS

| | | |
|---|---|---|
| 5,269,302 A | 12/1993 | Swartz et al. |
| 7,912,537 B2 | 3/2011 | Lee et al. |
| 8,112,148 B2 | 2/2012 | Giftakis et al. |

(Continued)

FOREIGN PATENT DOCUMENTS

| | | |
|---|---|---|
| AU | 2006242132 A1 | 11/2006 |
| EP | 1937141 A1 | 7/2008 |

(Continued)

OTHER PUBLICATIONS

Boon P, Vonck K. et al. A prospective, multicenter study of cardiac-based seizure detection to activate vagus nerve stimulation. Seizure 2015;32:52-61. 10.1016/j.seizure.2015.08.011.

(Continued)

*Primary Examiner* — Manuel L Barbee
(74) *Attorney, Agent, or Firm* — Young Basile Hanlon & MacFarlane, P.C.

(57) ABSTRACT

Systems, methods, and an event detection apparatus, for the detection of an imminent adverse physiological event, such as an epileptic seizure or cardiac event. Physiological state data can be generated based on at least one of pre-processed physiological state data, electrocardiogram (ECG) signals, and motion sensor signals. A plurality of features from the physiological state data can be extracted. The plurality of features can be classified based on a predetermined classifier. Responsive to the plurality of features corresponding to at least one of a plurality of adverse physiological event profiles, an adverse physiological event can be determined to be imminent.

20 Claims, 9 Drawing Sheets

(51) Int. Cl.
A61B 5/04 (2006.01)
A61B 5/00 (2006.01)

(52) U.S. Cl.
CPC ............ *A61B 5/721* (2013.01); *A61B 5/7267* (2013.01); *A61B 2562/0219* (2013.01)

(56) References Cited

U.S. PATENT DOCUMENTS

| | | |
|---|---|---|
| 8,983,591 B2 | 3/2015 | Leininger et al. |
| 9,060,729 B2 | 6/2015 | Kawamura |
| 2006/0111644 A1* | 5/2006 | Guttag .................... A61B 5/048 600/544 |
| 2013/0231580 A1* | 9/2013 | Chen ...................... A61B 5/7267 600/544 |
| 2014/0031635 A1* | 1/2014 | Sabesan ................ A61B 5/7282 600/301 |
| 2015/0157252 A1* | 6/2015 | Sabesan ................ A61B 5/4094 600/301 |

FOREIGN PATENT DOCUMENTS

| | | | | |
|---|---|---|---|---|
| WO | WO 2006119344 A2 | * | 11/2006 | ........... A61B 5/0024 |
| WO | WO-2006119344 A2 | * | 11/2006 | ........... A61B 5/0024 |
| WO | WO 2007040645 A1 | * | 4/2007 | ........... A61B 5/0002 |

OTHER PUBLICATIONS

Greene, Barry R. et al. Combination of EEG and ECG for improved automatic neonatal seizure detection. Clinical neurophysiology 118, No. 6 (2007): 1348-1359.

Hunyadi B., Signoretto M. et al. 2012. Incorporating structural information from the multichannel EEG improves patient-specific seizure detection. Clin Neurophysiol. 123(12), 2352-61.

Kramer U. et al. A novel portable seizure detection alarm system: preliminary results. J Clin Neurophysiol 2011.

Massetani, Roberto et al. Alteration of cardiac function in patients with temporal lobe epilepsy: different roles of EEG?ECG monitoring and spectral analysis of RR variability. Epilepsia 38, No. 3 (1997): 363-369.

Mporas, Iosif et al. Online seizure detection from EEG and ECG signals for monitoring of epileptic patients. In Hellenic Conference on Artificial Intelligence, pp. 442-447. Springer International Publishing, 2014.

Nasehi S., Pourghassem H. 2012. Seizure Detection Algorithms Based on Analysis of EEG and ECG Signals: a Survey, Neurophysiology. 44(2), 174-186.

Osorio, I. et al. Extracerebral detection of seizures: a new era in epileptology?. Epilepsy & Behavior 22 (2011): S82-S87.

Poh, Ming-Zher et al. Convulsive seizure detection using a wrist?worn electrodermal activity and accelerometry biosensor. Epilepsia 53, No. 5 (2012): e93-e97.

Ubeyli, E. D. (2009a). Combined neural network model employing wavelet coefficients for EEG signals classification. Digital Signal Processing, 19, 297-308.

Valderrama, M. et al. Patient specific seizure prediction using a multi feature and multi-modal EEG-ECG classification. XII Mediterranean Conference on Medical and Biological Engineering and Computing 2010, pp. 77-80.

Van de Vel A et al. Non?EEG seizure?detection systems and potential SUDEP prevention: State of the art. Seizure. Mar. 15, 2013.

* cited by examiner

ADVERSE PHYSIOLOGICAL EVENTS DETECTION

TECHNICAL FIELD

The present disclosure relates in general to methods, apparatuses, and systems for the detection of adverse physiological events.

BACKGROUND

Monitoring physiological states, including neurological or cardiac states, often takes place in a hospital or clinical setting. Further, the monitoring is commonly performed on a static patient connected to bulky, immobile equipment, and often operated by a specially trained technician. As the population grows more health conscious, there is an increasing demand for an effective way to monitor medically significant data outside of a clinical environment.

SUMMARY

Disclosed herein are aspects of implementations of methods, apparatuses, and systems for the detection of imminent adverse physiological events.

In an aspect, a method for detection of adverse physiological events using a wearable event detection apparatus comprises: generating, by the wearable apparatus, physiological state data based on at least one of pre-processed physiological state data, electrocardiogram (ECG) signals, and motion sensor signals; extracting, by the wearable apparatus, a plurality of features from the physiological state data; classifying, by the wearable apparatus, the plurality of features based on a predetermined classifier; and responsive to the plurality of features corresponding to at least one of a plurality of adverse physiological event profiles, determining, by the wearable apparatus, that an adverse physiological event is imminent.

In another aspect, a wearable adverse physiological event detection apparatus comprises a sensor configured to detect motion or ECG signals, a memory, and a processor configured to execute instructions stored in the memory to generate physiological state data based on at least one of pre-processed physiological state data, ECG signals, and motion sensor signals; extract a plurality of features from the physiological state data; classify the plurality of features based on a predetermined classifier; and responsive to the plurality of features corresponding to at least one of a plurality of adverse physiological event profiles, determine, that an adverse physiological event is imminent.

In another aspect, an adverse physiological event detection system comprises: a computing device; and a wearable event detection apparatus comprising a sensor configured to detect ECG signals or motion, a communication component configured to exchange signal data with the computing device, a non-transitory computer readable memory, and a processor configured to execute instructions stored in the non-transitory computer readable memory to: generate physiological state data based on at least one of pre-processed physiological state data, ECG signals, and motion sensor signals; extract a plurality of features from the physiological state data; classify the plurality of features based on a predetermined classifier; and responsive to the plurality of features corresponding to at least one of a plurality of adverse physiological event profiles, determine, that an adverse physiological event is imminent.

Details of these implementations, modifications of these implementations and additional implementations are described below.

BRIEF DESCRIPTION OF THE DRAWINGS

The disclosed technology is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
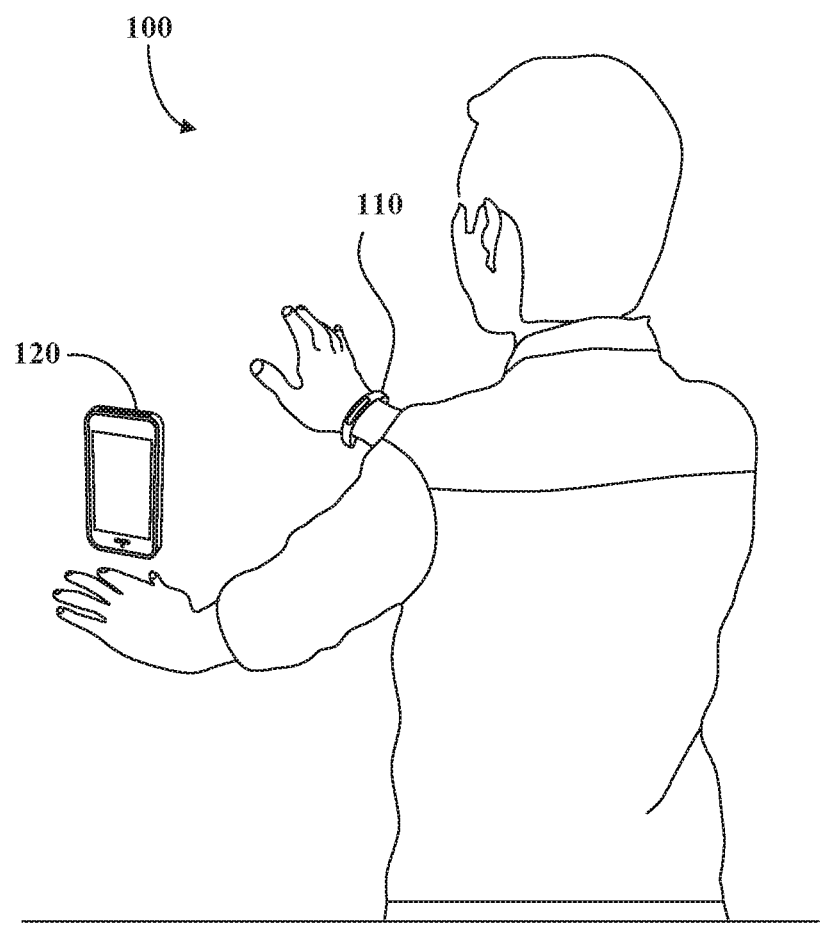
FIG. 1 is an illustration showing an implementation of an adverse physiological event detection apparatus in use.

The methods, apparatuses, and systems of the present disclosure address ways of dealing with problems particular to the field of adverse physiological event detection, including the use of a seizure management apparatus to facilitate detection of seizures.

Adverse physiological events, such as epileptic seizures and cardiac arrest, are often preceded by a change in the physiological state of an individual. These changes indicate that the adverse physiological event is imminent and detection of these changes can provide the afflicted individual with additional time to manage the event.

For example, an epileptic seizure can be preceded or accompanied by changes in electrical activity in the brain that can be detected by an electroencephalogram (EEG). Detecting these changes would give the epileptic individual additional time to more safely manage the seizure by, for example, moving from a standing position to sitting in a chair, or safely driving a vehicle to the side of a roadway to avoid the seizure occurring while driving. However, the equipment used to monitor physical states is often bulky, can often involve time-consuming set-up (e.g., positioning electrodes for an EEG), and the results generated by such equipment often involve analysis by a specialist (e.g., EEG analysis by a neurologist)

Attempts have been made at providing a portable way to monitor vital signs (e.g., indicators of bodily functioning such as body temperature, pulse rate, respiration rate, and blood pressure). For example, fitness tracking devices can monitor vital signs such as heart rate and output the heart rate data to a display device. However, fitness tracking devices that use a single vital sign have limited applicability, since heart rate data relates to but one of many vital signs that can be used to monitor an individual's health and determine when an adverse physiological event will occur. Moreover, though heart rate data can be used in isolation, and can be dispositive for some medical conditions, it is of limited use in analyzing other medical conditions. It is clear that the efficacy of predicting an adverse physiological event can be improved by drawing data from a variety of sources including electrocardiograms, electroencephalograms, and motion sensors.

Accordingly, it would be advantageous to be able to have a convenient way of detecting an imminent adverse physiological state in order to alert an individual that the adverse physiological event is imminent. Moreover, the user of an adverse physiological event apparatus could benefit from the device being portable and able to measure a variety of physiological signals such as electrocardiogram (ECG) signals and motion sensor data, while also leveraging the advantages of previously generated data that could be used to reconstruct an EEG signal based on the ECG signals.

The disclosed technology can leverage big data and deep learning networks to analyze the relationship between abnormal electrical activity in the brain (such as can be detected by an EEG) and other physical indicators such as electrical cardiac activity that can be monitored by an ECG. Further, the disclosed technology can monitor ECG signals, motion sensor signals, and other signals on a continuous basis. In this way a comprehensive snapshot of a user's physiological state can be generated and an imminent adverse physiological event, such as an epileptic seizure, can be more effectively detected.

The methods, apparatuses, and systems of the present disclosure address ways of dealing with problems particular to the field of adverse physiological event detection, including the use of an apparatus such as a wearable adverse physiological event apparatus to facilitate detection of adverse physiological events.

FIG. 1 is a diagram of an implementation of a wearable system 100 which can include a wearable apparatus 110 worn by an individual and a device core 120. The wearable apparatus 110 can include a housing that is in the form of a ring, bracelet, wristband, pendant, armband, anklet, headband, belt, necklace, glove, a chest patch, or other mechanism for securing or attaching the wearable apparatus 110 to a human body.

According to an implementation, the wearable apparatus 110 can include one or more processing cores (not shown) that are configured to receive signals from sensors (not shown) that can include one or more electrodes, to detect or determine the state or condition of a human body to which the wearable apparatus 110 is secured or in contact with. The wearable apparatus 110 can include an ECG component, such as an ECG sensor that can include multiple electrodes for measuring electrical activity produced by the heart, which can be used to determine heart rate and other indicators of heart function that can be used to determine when an adverse physiological event is imminent.

For example, the wearable apparatus 110, can detect the heart rate or hand movements of an individual wearing the wearable apparatus 110. By comparing features extracted from captured data based on measured a heart rate or hand movements, to profile data that includes profiles of adverse physiological events, the wearable apparatus 110 can determine when an adverse physiological event, including an epileptic seizure or stroke, is imminent.

Further, the wearable apparatus 110 can exchange (send or receive) data from a remote data source. For example, a health profile of a user, including measurements (e.g., ECG measurements) from the wearable apparatus 110, can be sent to a remote cloud server where the measurements can be stored for later retrieval and use.

Though illustrated as a single device, the wearable apparatus 110 can be part of a wearable system 100 which can be multiple devices including a device such as the device core 120, which can be used to exchange physiological state data with the wearable apparatus 110 or with a remote computing device such as a server device (not shown) that can store data including physiological state data, and adverse physiological event data.

For example, the wearable apparatus 110 can include a chest patch (not shown), which can be attached to the chest of the individual, and device core 120 which can be attached and removed from the chest patch. The chest patch can be, for example, an adhesive patch, a sticker, or the like. When attached to the chest of the individual, the first electrode of the ECG sensor on the interior surface facing the skin of the individual can be in contact with the skin of in the area of the chest of the individual, which can form the lead to generate the electronic signals for heart activity measurements (e.g., ECG measurements). For example, the electrode can include one or more leads.

The wearable apparatus 110 can alert an individual when an adverse physiological event is imminent by generating an indication, such as a visual, audible, or haptic indication. In this way, an individual can take appropriate actions (e.g., seeking medical assistance) when the indication is generated.

Figure 2:
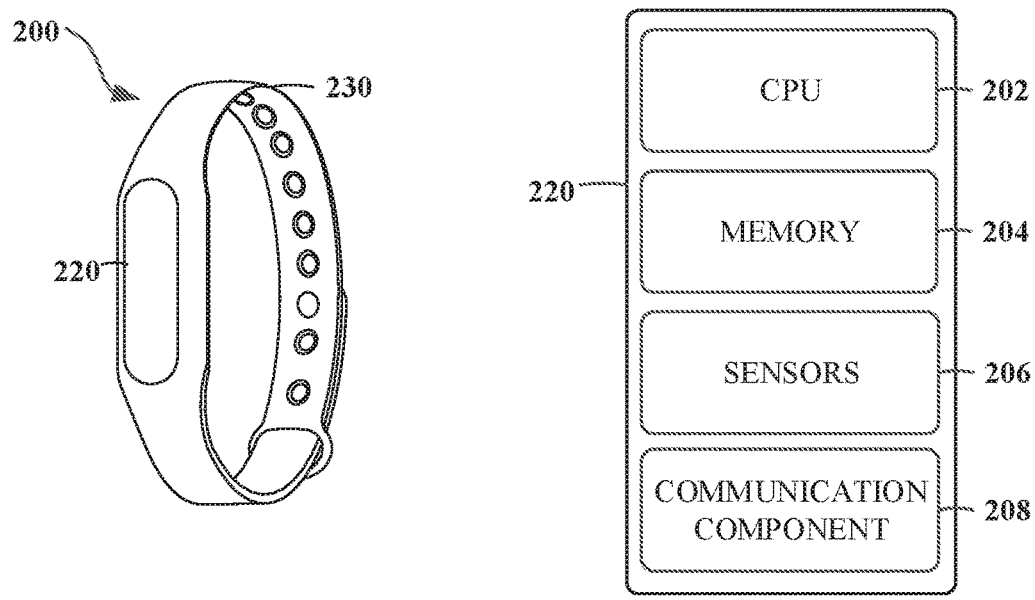
FIG. 2 is a diagram of an implementation of a wearable adverse physiological event detection apparatus usable within implementations of the disclosure.

FIG. 2 is a diagram of an implementation of a wearable apparatus 200 usable within implementations of the disclosure. The wearable apparatus 200 can be a wearable device such as the wearable apparatus 110 discussed above with respect to FIG. 1. For example, the wearable apparatus 200 can include a device core 220 and one or more accessory components including a housing, such as a band 230 or a chest patch (not shown).

In an implementation, the device core 220 can include a central processing unit (CPU) 202, a memory 204, sensors 206, and a communications component 208. The CPU 202 can include single or multiple processors each having single or multiple processing cores. Alternatively, the CPU 202 can include another type of device, or multiple devices, capable of manipulating or processing data.

The memory 204 can comprise random access memory device (RAM) or any other suitable type of storage device such as a non-transitory computer readable memory. The memory 204 can include executable instructions and data that can be accessed by the CPU 202, for example, data generated or processed in signals received from the sensors 206. The memory 204 can include one or more DRAM modules such as double data rate synchronous dynamic random-access memory (DDR SDRAM). The memory 204 can include another type of device, or multiple devices, capable of storing data for retrieval or processing by the CPU 202. The CPU 202 can access and manipulate data in stored in the memory 204 via a bus.

The sensors 206 can include one or more sensors that can be disposed on any part of the wearable apparatus 200. The sensors 206 can be used to identify, detect, determine, or generate signal data indicative of measurements (e.g., electrical activity or motion) associated with the wearable apparatus 200 or an individual wearing the wearable apparatus 200.

The sensors 206 can include one or more sensors used to detect the state or condition of an environment, including electromyography sensors, accelerometers, gyroscopes, optical sensors, light emitters, microphones, or touch sensors. The accelerometers can include various numbers of axes including a three-axis, a six-axis, or a nine-axis accelerometer. The optical sensors can include RGB cameras, infrared cameras, monochromatic infrared cameras, or any other optical sensor that can capture still images or moving images. The light emitters can be infrared light emitting diodes (LED), infrared lasers, or any other suitable lights. The sensors 206 can include one or more sensors that can generate heart activity signals such as an EEG sensor, a photoplethysmogram (PPG) sensor, an electromyogram (EMG) sensor, or the like.

For example, the ECG sensor can comprise a first electrode arranged in an interior surface of device core 220, which can be positioned to be in contact with the skin of an individual when worn, and a second electrode arranged in an exterior surface of the device core 220. The sensors 206 can include sensors capable of generating biometric signals, such as ECG signals, through non-invasive techniques which do not penetrate or contact the skin of the individual.

The sensors 206 can also comprise one or more bioimpedance sensors, microphones, temperature sensors, touch screens, finger readers, iris scanners, a combination of the above, or the like. Implementations of the sensors 206 can include a single sensor, one of each of the foregoing sensors, or any combination of the foregoing sensors. In an implementation, the signal data can be identified, detected, determined, or otherwise generated based on any single sensor or combination of sensors included in the wearable apparatus 200.

The communications component 208 can be a hardware or software component configured to communicate data, such as measurements of vital signs, from the sensors 206 to one or more external devices, such as another wearable device or a computing device, for example. In an implementation, the communications component 208 comprises an active communication interface, for example, a modem, transceiver, transmitter-receiver, or the like. In an implementation, communications component 208 comprises a passive communication interface, for example, a quick response (QR) code, Bluetooth identifier, radio-frequency identification (RFID) tag, a near-field communication (NFC) tag, or the like. The communication component 208 can operate over wired or wireless communication connections, such as, for example, a wireless network connection, a Bluetooth connection, an infrared connection, an NFC connection, a cellular network connection, a radio frequency connection, or any combination thereof. In some implementations, the communication component 208 can use sound signals as input and output, such as, for example, an ultrasonic signal or a sound signal via an audio jack. Implementations of the communications component 208 can include a single component, one of each of the foregoing types of components, or any combination of the foregoing components.

The wearable apparatus 200 can also include other components not shown in FIG. 2. For example, the wearable apparatus 200 can include one or more input/output devices, such as a display. In an implementation, the display can be coupled to the CPU 202 via a bus. In an implementation, other output devices can be included in addition to or as an alternative to the display. When the output device is or includes a display, the display can be implemented in various ways, including by an LCD, CRT, LED, OLED, or other device capable of displaying a still or moving image. In an implementation, the display can be a touch screen display configured to receive touch-based input, for example, in manipulating data output to the display.

Figure 3:
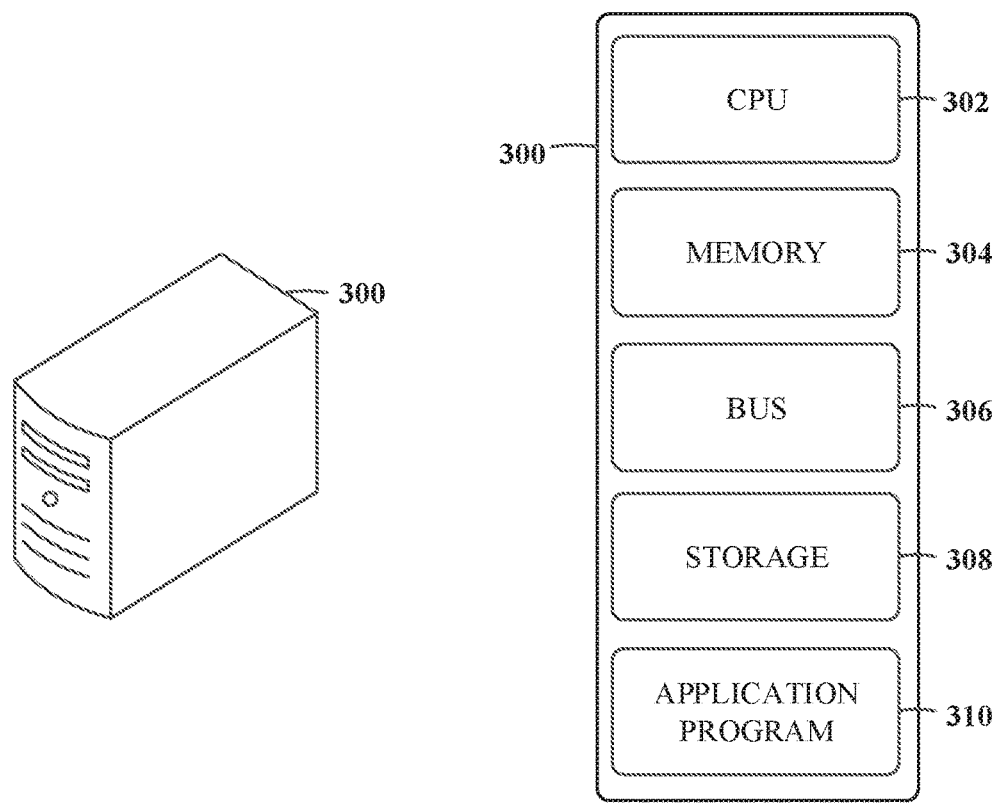
FIG. 3 is a diagram of an implementation of a computing device usable within implementations of the disclosure.

FIG. 3 shows a computing device 300 for example and a block diagram of a hardware configuration of the computing device 300 according to implementations of this disclosure. Computing device 300 can be a part of the system for detection of adverse physiological events disclosed herein. In some implementations, the computing device 300 and the wearable apparatus 200 (or any device having measurement capabilities) can be the same device. The computing device 300 can be shown for example type of computer in FIG. 3, and is not limited to any specific type or any specific quantity in the system disclosed herein. The computing device 300 can be implemented by any configuration of one or more computers, such as a microcomputer, a mainframe computer, a super computer, a general-purpose computer, a special-purpose/dedicated computer, an integrated computer, a database computer, a remote server computer, a personal computer, a laptop computer, a tablet computer, a cell phone, a personal data assistant (PDA), a wearable computing device, e.g., a smart watch, or a computing service provided by a computing service provider, e.g., a website, or a cloud service provider. In some implementations, the computing device 300 can be a smart phone device that can be used to display and analyze ECG signals. In some implementations, certain operations described herein can be performed by a computer (e.g., a server computer) in the form of multiple groups of computers that are at different geographic locations and can or cannot communicate with one another by way of, such as, a network. While certain operations can be shared by multiple computers, in some implementations, different computers can be assigned with different operations.

The computing device 300 can include at least one processor such as the CPU 302. CPU 302 as well as the CPU 202 can be any type of device, or multiple devices, capable of manipulating or processing information. Although the examples herein can be practiced with a single processor as shown, advantages in speed and efficiency can be achieved using more than one processor. CPU 302 can be distributed across multiple machines or devices (each machine or device having one or more of processors) that can be coupled directly or across a local area or other network. Although the examples herein can be practiced with a single processor as shown, advantages in speed and efficiency can be achieved using more than one processor.

The memory 304 as well as memory 204 can be, for example, a random access memory device (RAM), a read-only memory device (ROM), an optical disc, a magnetic disc, or any other suitable type of storage device, and can store code and data that can be accessed by CPU 302 using a bus 306. Although one of the bus 306 is depicted, multiple buses can be utilized. The memory 304 can be distributed across multiple machines or devices such as network-based memory or memory in multiple machines performing operations that can be described herein as being performed using a single computing device for ease of explanation. The code can include an operating system and one or more application program 310 processing and/or outputting the data. As will be discussed in detail below, the application program 310 can include software components in the form of computer executable program instructions that cause the CPU 302 to perform some or all of the operations and methods described herein. In some implementations, the computing device 300 is used to implement computing device 300 or at least an analysis component of the computing device 300, in which application program 310 stored by memory 304 can implement some or all of the processes as described in more detail below.

The computing device 300 can optionally include a storage device 308 in the form of any suitable non-transitory computer readable medium, such as a hard disc drive, a memory device, a flash drive or an optical drive. The storage device 308, when present, can provide additional memory when high processing requirements exist. The storage device 308 can also store any form of data, relating or not relating to cardiac information. Further, storage device can be a component of the computing device 300 or can be a shared device that is accessed via a network.

The computing device 300 can include more devices or components. For example, computing device can further include one or more input devices, output devices, communication devices, or any other device that can be used to transmit, store, process, and present data.

Although FIG. 3 depicts a hardware configuration that can implement a computing device 300, other configurations can be utilized. The hardware configuration of a computing system as depicted in an example in FIG. 3 thus can be implemented in a wide variety of configurations.

Figure 4:
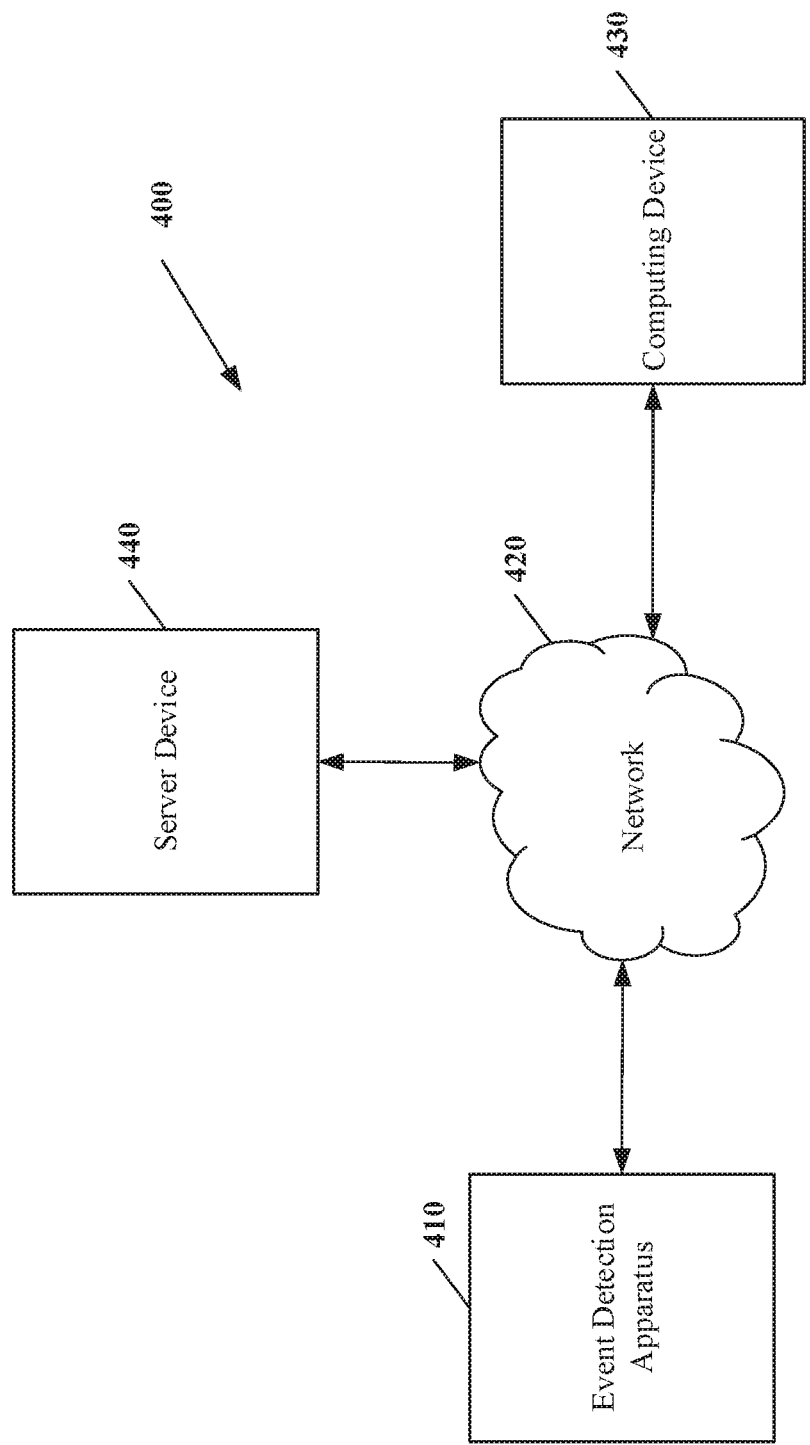
FIG. 4 is a diagram of system for detection of an adverse physiological event including computing devices in a network environment according to implementations of this disclosure.

FIG. 4 is a system diagram including a network environment 400 that incorporates a wearable event detection apparatus 410, which in an implementation can include the features of the wearable apparatus 200 illustrated in FIG. 2. In an implementation, the wearable event detection apparatus 410 is coupled, via the network 420, to: computing device 430, which in an implementation can include the features of the computing device 300 illustrated in FIG. 3; and server device 440 which in an implementation can include the features of a data server computing device configured to exchange (send and receive) data with requesting client devices such as the computing device 430. The network environment 400 is not limited to the illustrated topology and the wearable event detection apparatus 410 can be coupled to other devices via other topologies.

The wearable event detection apparatus 410, the computing device 430, and the server device 440 can communicate via the network 420, which can include one or more communications networks of any suitable type in any combination of wired or wireless networks, including local area networks (LAN), wide area networks (WAN), cellular data networks, and the Internet. When more than one of the wearable event detection apparatus 410 is used, each wearable event detection apparatus 410 can be connected to the same network or to different networks.

For example, the wearable event detection apparatus 410 can measure or store data including physiological state data (e.g., ECG data), which can be sent to the computing device 430 or the server device 440. Further, the wearable event detection apparatus 410 can receive data, including adverse physiological event profiles or individualized physiological state data that can be stored remotely, such as on the server device 440. In an implementation, data from the wearable event detection apparatus 410 can be stored in a remote computing device such as a cloud storage device.

Figure 5A:
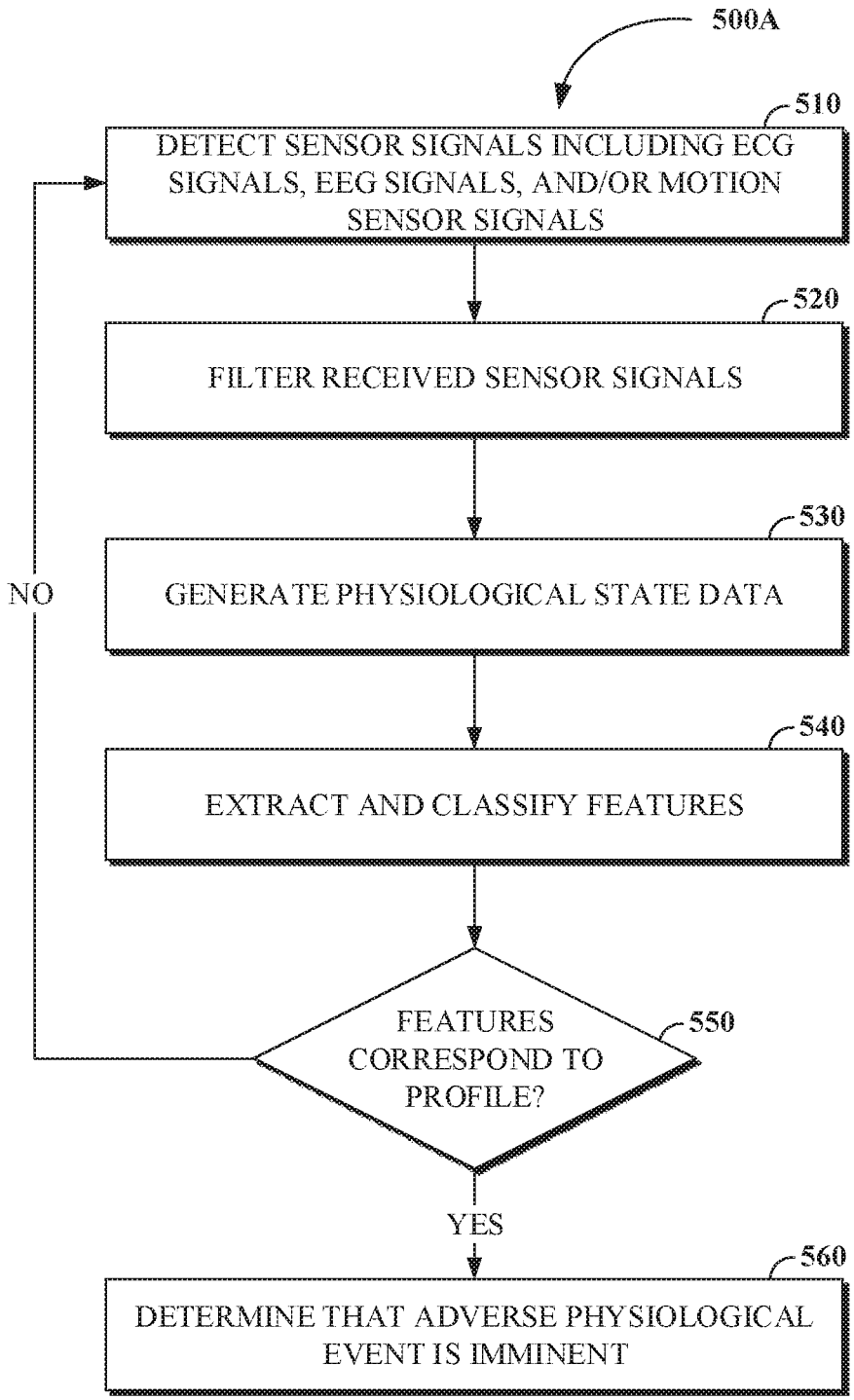
FIG. 5A is a flow diagram showing an implementation of a method for detecting an adverse physiological event according to implementations of this disclosure.

FIG. 5A is a flow diagram showing an example process 500A for detection of adverse physiological events according to implementations of this disclosure. In some implementations, the process 500A can be implemented in a device or apparatus such as: the wearable apparatus 110, shown in FIG. 1, the wearable apparatus 200 shown in FIG. 2, or the computing device 300 in FIG. 3. In some implementations, some of the operations of the method 600 can be performed by a computing device such as the computing device 430 or the server device 440 shown in FIG. 4.

At operation 510, sensor signals, including at least one of ECG signals, EEG signals, and motion sensor signals are detected. For example the detection of the signals can be performed by sensors such as the sensors 206 illustrated in FIG. 2.

The ECG signals can indicate electrical activity that is produced by a heart including the frequency or the amplitude of the signals. For example, the ECG signals can include at least one of: heart rate; PQRST cycle; and stroke volume. The EEG signals can indicate electrical activity that is produced by a brain. The motion sensor signals can indicate movement including changes in an orientation, direction, position, acceleration, or velocity of the sensor or an object in contact with a sensor such as the sensor 206. For example, the motion sensor signals can include signals from at least one of an accelerometer (e.g., accelerometer signals), a gyroscope (e.g., gyroscope signals), and an inertia measurement unit (IMU) (e.g., IMU signals).

At operation 520, the sensor signals, including at least one of the ECG signals, EEG signals, and the motion sensor signals can be filtered to produce respective filtered ECG signals, filtered EEG signals, or filtered motion sensor signals.

Filtering the signals can include the minimization of features, such as noise or interference that change signals including at least one of ECG signals, EEG signals, and the motion sensor signals. For example, changes in the signals that can be reduced by filtering include changes that obscure, interfere with, weaken, or amplify, the signals.

For example, the noise can include at least one of: ECG noise, including electrical activity that changes or disrupts the ECG signals; EEG noise, including electrical activity that changes or disrupts the EEG signals; and motion sensor noise, including vibrations that change or disrupt the motion sensor signals.

The filtering can be used to extract data from the ECG signals and the EEG signals based on an adverse physiological event frequency band, such as an epilepsy-related frequency band. The filtering can include at least one of: powerline notch filtering; bandpass filtering; wandering baseline removal; adaptive exponential filtering; and adaptive smooth filtering. The bandpass filter can extract information within a frequency band of an EEG signal related to an adverse physiological event (e.g., epilepsy). The noise and wandering baseline in an ECG signal can be reduced by going through the powerline notch filter, the bandpass filter, the wandering baseline remover, and a novel adaptive exponential filter.

For example, an electrical power source such as a computing device, can produce noise that interferes with signals such as ECG signals. Filtering can reduce the noise so that the ECG signal is more similar (e.g., similarity can be in terms of the amplitude and frequency of the ECG signal) to the ECG signal without the electrical interference. As a further example, filtering noise from the motion sensor signals can include minimizing the noise from vibrations produced by a mechanical device that is in direct or indirect contact with the motion sensor. Filtering can improve the later extraction of features from data such as physiological state data that is based on the signals.

In an implementation, the ECG signals or the motion sensor signals can pass through a filter that does not change the ECG signals or the motion sensor signals. In this way, the raw ECG signals or raw motion sensor signals can be used as the basis for generating physiological state data.

At operation 530, data including physiological state data is generated. The physiological state data can be based on at least one of pre-processed physiological state data, the ECG signals, and the motion sensor signals.

The pre-processed physiological state data can include at least one of: aggregate EEG data based on a plurality of aggregate EEG signals received over a plurality of time intervals; aggregate ECG data based on a plurality of aggregate ECG signals over the plurality of time intervals; and aggregate motion sensor data based on a plurality of aggregate motion sensor signals over the plurality of time intervals.

The pre-processed physiological state data can be based on measurements from a single individual or a plurality of individuals, including multiple measurements taken from the same individual at different times or multiple measurements from different individuals at the same time or at different times. In an implementation, the pre-processed physiological state data can be based on predetermined data that can be generated during one or more off-line training sessions or on-line training sessions.

The pre-processed physiological state data can include EEG reconstruction data that can be generated based on a comparison between the aggregate EEG data and at least one of the aggregate ECG data or the aggregate motion sensor data. The EEG reconstruction data can include data relating to correlations between the aggregate EEG data and the aggregate ECG data or the aggregate motion sensor data. For example, eccentric leg movement, detectable by a motion sensor in a wearable apparatus, such as the wearable apparatus 200, can correspond to neurological activity indicative of an imminent adverse physiological event including an epileptic seizure.

Machine learning algorithms, including neural networks such as a convolutional neural network (CNN), or linear regression model can be used to generate reconstructed EEG data based on correlations between the aggregate EEG data and at least one of the aggregate ECG data and the aggregate motion sensor data. Further, access to big data and physiological feature extraction methods can be used for feature extraction.

The correlations between the aggregate EEG data and at least one of the ECG signals and the motion sensor signals can be used to reconstruct the EEG data in the absence of EEG signals. Moreover, learning algorithms can be used to reconstruct EEG features based on the ECG signals which can be facilitated through big data training (e.g., analysis, capture, search, and data processing of very large or complex datasets). In an implementation, the features can be extracted and analyzed within a predetermined time window size.

For example, the aggregate EEG data can include a plurality of datasets corresponding to a plurality of EEG outputs from an EEG (e.g., measured voltage fluctuations from the brain). The plurality of EEG outputs can be compared to: a plurality of ECG outputs; or a plurality of motion sensor outputs, that were contemporaneously measured with the plurality of EEG outputs. In an implementation, the pre-processed physiological state data can include the EEG reconstruction data.

At operation 540, a plurality of features is extracted from the physiological state data and classified based on a pre-determined classifier such as an adverse physiological event classifier. The classifier can include one or more classification models that can be used to receive an input, such as features of the physiological state data, and produce an output that classifies the features. For example, the classifier can include a support vector machines (SVM), a multi layer perceptron (MLP), a decision-tree classifier, a random decision forest classifier, or a naive Bayes classifier.

The adverse physiological event classifier can be based on a previously trained classification model that was trained using one or more machine learning techniques and data including the aggregate EEG data, the aggregate ECG data, or the aggregate motion sensor data. Further, the training of the classification model can be based on data stored on remote computing devices including cloud computing devices which can extract features from data gathered from a plurality of sources such as EEG data, EEG data, and motion sensor data from large population groups.

For example, the training of the previously trained classification model can include receiving input of EEG signals, ECG signals, and motion sensor signals that are indicative of an adverse physiological event including at least one of: a cardiovascular event such as a myocardial infarction; a neurological event such as an epileptic seizure; an ischemic event such as an ischemic stroke; a central nervous system event; and a hemorrhagic event (also known as a haemorrhagic event) such as a hemorrhagic stroke. The training can include weighting of the data which can be based on a pre-determined identification of features that are known to be significant with respect to the occurrence of an adverse physiological event.

At operation 550, a determination of whether the plurality of features that were extracted, corresponds to at least one of a plurality of profiles including a plurality of adverse physiological event profiles. The plurality of profiles can be based on data including at least one of the aggregate EEG data, the aggregate ECG data, the aggregate motion sensor data, and adverse physiological event attributes that can indicate attributes or characteristics of an adverse physiological event (e.g., an elevated heart rate preceding an adverse cardiac event). The plurality of profiles can include profiles for various diseases or adverse physiological events.

The plurality of profiles can include profile data that can include at least one of: pre-determined data, such as data extracted from an offline training process; local data, such as data collected by an apparatus, such as the wearable apparatus 200; and remote data, including data stored on a remote server device such as a cloud server.

The plurality of profiles can be associated with: an adverse physiological event such as an epileptic seizure or cardiac arrest; or an individual, including physiological states or conditions of the individual such as baseline physiological states or adverse event physiological states. For example, the plurality of profiles can include features or characteristics of an adverse physiological event based on the physiological state data and the pre-processed physiological state data.

Based on a determination that the plurality of features does not correspond to or not match at least one of a plurality of adverse physiological event profiles, process 500A goes back to operation 510. Based on a determination that the plurality of features correspond to or match at least one of the plurality of adverse physiological event profiles, process 500A proceeds to operation 560.

At operation 560, an adverse physiological event is determined to be imminent. For example, the determination of an adverse physiological event can include an indication that the physiological event is imminent.

Figure 5B:
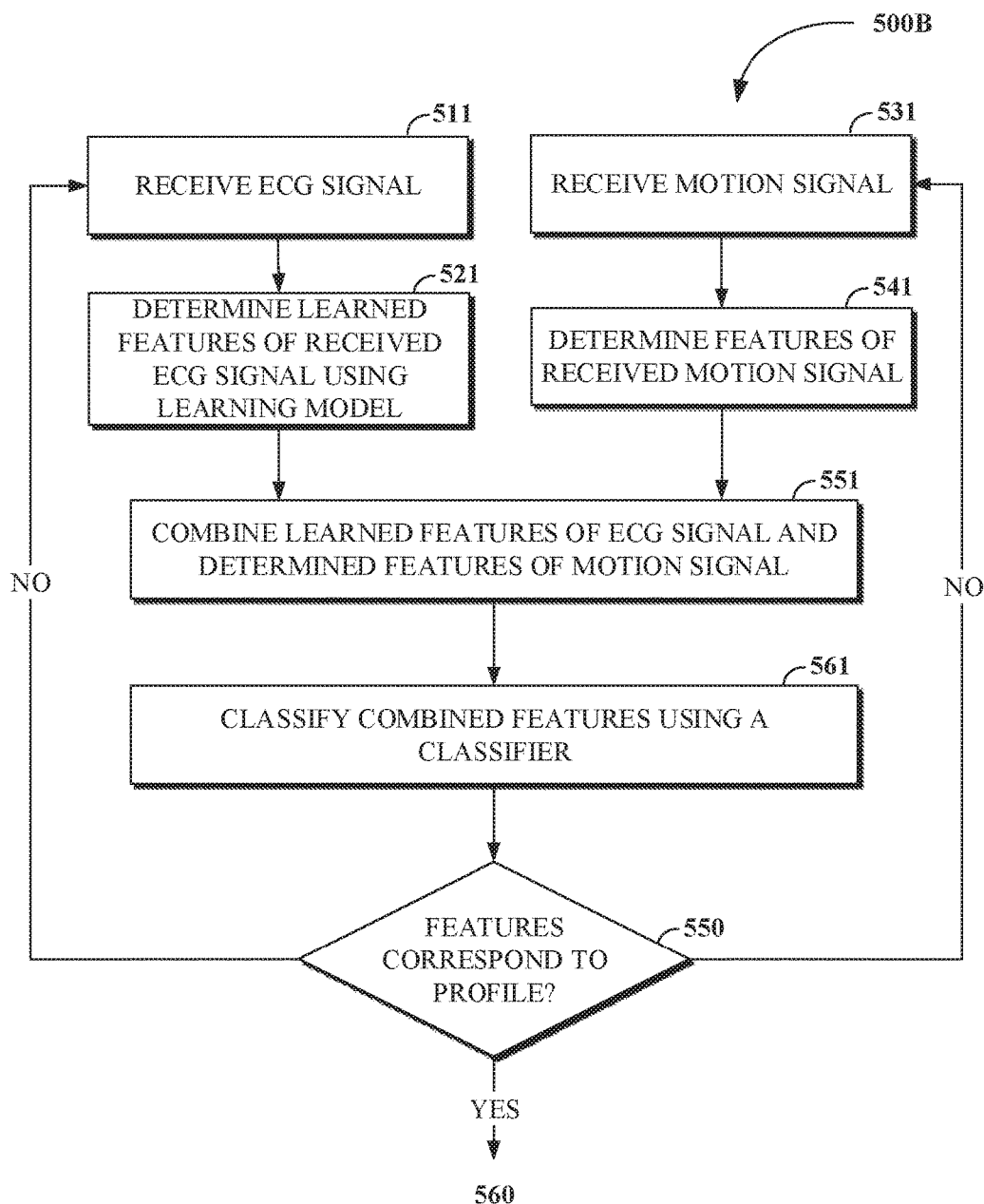
FIG. 5B is a flow diagram showing an implementation of a method for detection of adverse physiological events according to implementations of this disclosure.

FIG. 5B is a flow diagram showing another example process 500B for detection of adverse physiological events according to implementations of this disclosure. In some implementations, the process 500B can be implemented in a device or apparatus such as the wearable apparatus 110 shown in FIG. 1, the wearable apparatus 200 shown in FIG. 2, or the computing device 300 shown in FIG. 3.

At operation 511, an ECG signal is received. This operation is similar to operation 510 in FIG. 5A. For example, the ECG signal can be received by sensors such as the sensors 206 illustrated in FIG. 2. The term "receive" used herein can refer to receiving, inputting, acquiring, retrieving, obtaining, reading, accessing, or any action in any manner for inputting information or data. The ECG signals can indicate electrical activity that is produced by a heart including the frequency or the amplitude of the signals.

At operation 521, feature data of the received ECG signal is determined. This operation is similar to operation 520 in FIG. 5A. Determining the feature data of the ECG signal can include minimization of feature data, such as noise or interference reduction. The feature data of the ECG signal can include time-domain feature data, such as, for example, a mean R-R interval (IRR), standard deviation of R-R intervals (rRR), a mean R-R interval spectral entropy (RRH), a mean change in the R-R intervals (DRR), an R-R interval coefficient of variation (dRR), an R-R interval power spectral density (RRPSD), or an R-R interval Low-High frequency power ratio. The feature data of the ECG signal can include frequency-domain feature data, such as, for example, a low frequency ratio, a high frequency ratio, or parameters and outputs from a Fast Fourier Transform (FFT), a wavelet transform (WT), or a combination of an autocorrelation and a discrete cosine transform (AC-DCT). The feature data of the ECG signal can include learned feature data obtained as outputs of a learning model, such as a machine learning model (e.g., a convolutional neural network or a linear regression model). The learning model can use the ECG signal as input and be trained using feature data extracted from multiple EEG signals that indicate electrical activity produced by a brain of an individual. By using the learned feature data, accuracy of detection of the adverse physiological events can be increased. The feature data of the EEG signals can be based on measurements from a single individual or multiple individuals, including multiple measurements taken from the same individual at different times or multiple measurements from different individuals at the same time or at different times. In some implementations, the feature data of the EEG signals can be based on predetermined EEG feature data that can be generated during one or more off-line training sessions or on-line training sessions.

At operation 531, a motion signal associated with a movement is received. For example, the movement can be abnormal movements of legs and arms.

At operation 541, feature data of the received motion signal is determined. The feature data of the motion signal can include a mean and a standard deviation of motion amplitudes over certain time windows. For example, a current time can be designated as t(s); the x-, y-, and z-axis components of the motion sensor (e.g., an accelerometer) can be designated as ax(t), ay(t), and az(t) respectively; and a time window size can be designated as L. Two example features, a mean ($\bar{a}$) and a standard deviation ($\sigma_{\bar{a}}$) of the motion sensor within the time window size L, can then be represented as:

$$\bar{a} = \frac{1}{L} \sum_{i=t-L+1}^{t} (ax(i)^2 + ay(i)^2 + az(i)^2) \text{ where } (L = 15, 30, 45)$$

$$\sigma_{\bar{a}} = \text{var}(ax(t-60:t)^2 + ay(t-60:t)^2 + az(t-60:t)^2)$$

At operation 551, the feature data of the ECG signal and the feature data of the motion signal are combined. By combining the feature data of the ECG and motion signals, the accuracy of detection of the adverse physiological events can be further increased. In some implementations, the combined feature data can be represented by a feature vector. In some implementations, the combined feature data can include the EEG reconstruction data.

At operation 561, the combined feature data is classified using a classifier, such as an adverse physiological event classifier. Following operation 561, the process 500B proceeds to operation 550, which is the same as the operation 550 in FIG. 5A.

Figure 6:
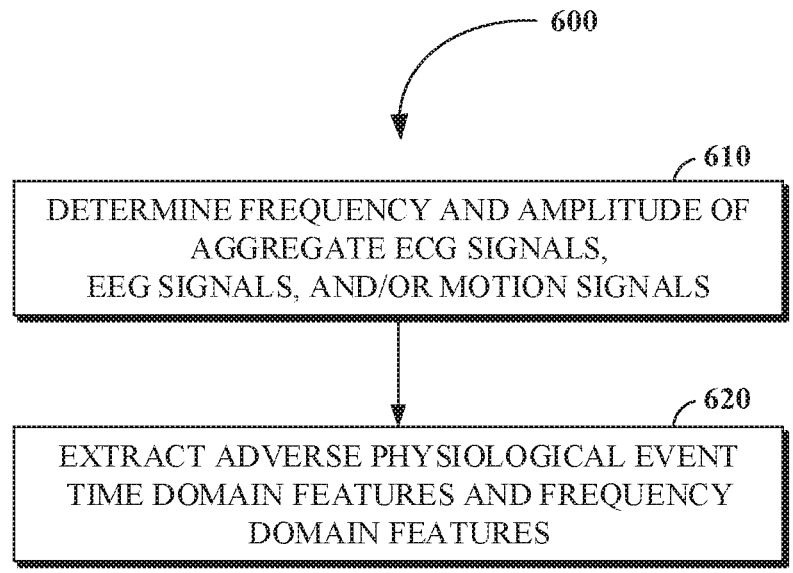
FIG. 6 is a flowchart showing an implementation of a method for extracting frequency domain features and time domain features from physiological state data according to implementations of this disclosure.

Based on a determination that the plurality of features does not match at least one of a plurality of adverse physiological event profiles, process 500A goes back to operation 511 and/or 531. Based on a determination that the plurality of features matches at least one of the plurality of adverse physiological event profiles, process 500A proceeds to operation 560 in process 500A. FIG. 6 is a flow chart of an example method 600 for detection of adverse physiological events. Implementations of the method 600 can be performed by an apparatus such as the wearable apparatus 200 shown in FIG. 2 or the computing device 300 in FIG. 3. In some implementations, some of the operations of the method 600 can be performed by a computing device such as the computing device 430 or the server device 440 shown in FIG. 4.

At operation 610, the wearable apparatus 200 can determine a frequency and amplitude of at least one of: the aggregate ECG signals, the EEG signals, and the motion sensor signals. In other examples, the frequency and amplitude of at least one of the signals (e.g., aggregate ECG signals, the EEG signals, and the motion sensor signals) can be determined by another device, such as the computing device 300 shown in FIG. 3.

The frequency and amplitude of the aggregate ECG signals can include a: heart rate; PR interval; P duration; P amplitude; QRS duration; QRS amplitude; QT interval; RR interval; mean RR interval; RR standard deviation; RR interval spectral entropy; mean RR interval spectral entropy; mean change in the RR interval; standard deviations in the RR interval; RR interval coefficient of variation; RR interval power spectral density; RR interval low-high frequency power ratio; or one or more other characteristics of the PQRST cycle.

The frequency and amplitude of the EEG signals can include bands in different ranges including at least one of: an alpha band including a range of less than 4 Hz; a delta band including a range of 4-7 Hz; a theta band including a range of 8-15 Hz; a mu band including a range of 8-12 Hz; a beta band including a range of 8-31 Hz; and a gamma band in the range of 32 Hz and greater.

The frequency and amplitude of the motion sensor signals can include at least one of: a velocity or an acceleration of linear, rotary, reciprocating, and oscillating motion detected by a sensor such as the sensors 206.

At operation 620, adverse physiological event time-domain features and adverse physiological event frequency domain features are extracted based on the frequency and the amplitude of the aggregate ECG signals, the aggregate EEG signals, or the aggregate motion sensor signals.

The adverse physiological event time domain features can include features in a time domain representation of the signals including the ECG signals, the EEG signals, and the motion sensor signals. The adverse physiological event frequency domain features can include features in a frequency domain representation of the signal, including parameters and outputs from a Fast Fourier Transform (FFT), a wavelet transform (WT), or the combination of an autocorrelation and a discrete cosine transform (AC-DCT).

The above features can be combined in a single feature vector that is classified by a classifier (e.g., support vector machine, multiple layer perceptron, or random decision forest) to generate a final prediction result. In an implementation, optimized parameters in the classifier can be acquired in an offline training session.

Figure 7:
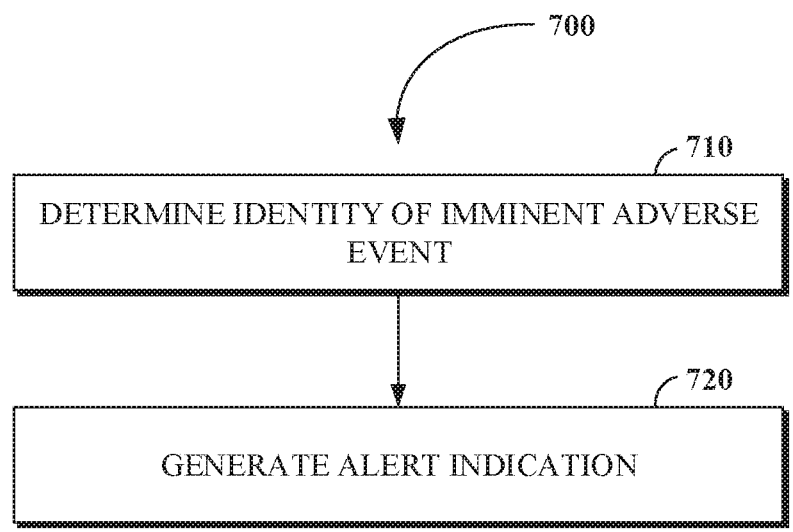
FIG. 7 is a flowchart showing an implementation of determining an identity of an adverse physiological event and generating an indication according to implementations of this disclosure.

FIG. 7 is a flow diagram of an example method 700 for detection of adverse physiological events. Implementations of the method 700 which can be performed by an apparatus such as the wearable apparatus 200 shown in FIG. 2 or the computing device 300 in FIG. 3.

At operation 710, an identity of the imminent adverse physiological event is determined based on a correspondence, such as matching, of at least one of the plurality of adverse event profiles to an associated adverse physiological event profile identity. For example, the matching of the plurality of adverse event profiles to the associated adverse physiological event profile identity can include using a lookup table.

At operation 720, an alert indication including the identity of the imminent adverse physiological event is generated. The alert indication can include at least one of a haptic alert, an audible alert, a visual alert, and an electronic message. For example, when an adverse physiological event is determined to be imminent an audible indication such as a chime can alert the wearer of a device such as the wearable apparatus 200 or the computing device 300. When the alert indication is an electronic message, the electronic message, which can include data packets or data signals, can be sent to a remote computing device, such as a server device, which can receive the electronic message and can subsequently perform an action such as contacting a designated medical services provider.

Figure 8A:
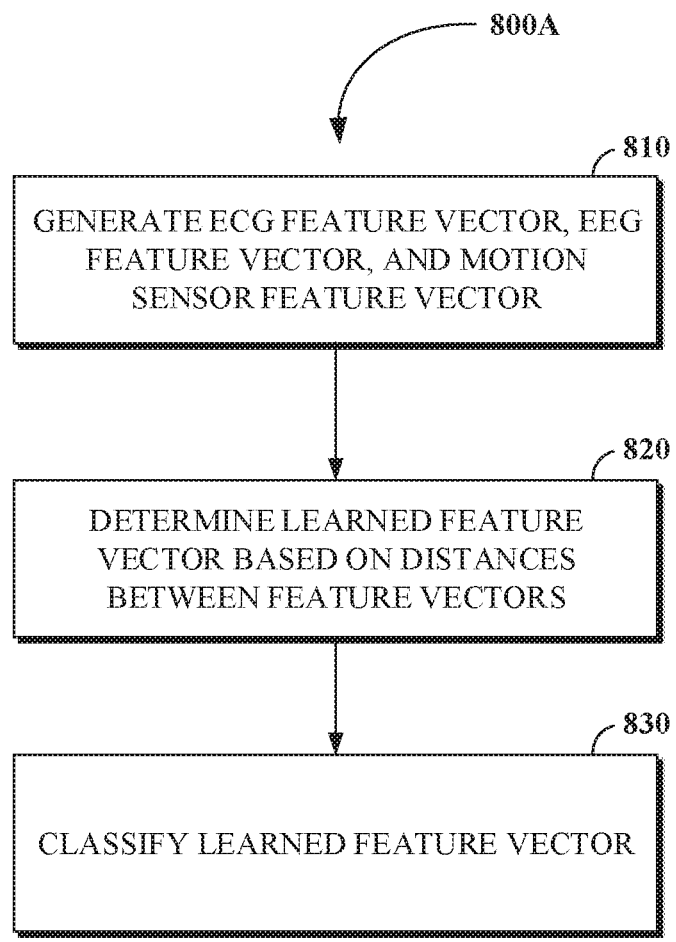
FIG. 8A is a flow diagram showing an implementation of a method for detecting an adverse physiological event according to implementations of this disclosure.

FIG. 8A is a flow diagram of an example method 800A for the detection of adverse physiological events according to implementations of this disclosure. Implementations of the method 800A which can be performed by an apparatus such as the wearable apparatus 200 shown in FIG. 2 or the computing device 300 in FIG. 3. In a further implementation, the method 800 can be performed offline (e.g., an offline learning network) by one or more computing devices.

At operation 810, one or more feature vectors is generated including at least one of: an EEG feature vector based on data based on EEG signals such as the aggregate EEG data; an ECG feature vector based on data including ECG signals such as the aggregate ECG data; and a motion sensor feature vector based on data including motion sensor data such as the aggregate motion sensor data. In an implementation, the generation of the one or more feature vectors can be performed: on a local device, such as the wearable apparatus 200 or the computing device 300; or in an offline learning network. The one or more feature vectors can include attributes and corresponding values. For example, an ECG feature vector can include heart rate values and other features of ECG signals. Further, adverse physiological event features such as epilepsy related features (e.g., high frequency power) can be extracted from the EEG signals.

At operation 820, a learned feature vector is generated based on a distance, including a Euclidean distance (e.g., an $L^2$ distance), between the EEG feature vector and the ECG feature vector or the motion sensor feature vector. For example, the learned feature vector can be used to predict EEG features at points in an electrocardiogram.

The distance (e.g., $L^2$ distance) between the EEG feature vector and the ECG feature vector or the motion sensor feature vector can be used as a regularization term in cost function used to determine the learned feature vector.

For example, a learning network, such as a convolutional neural network (CNN) can convolute the ECG data points N into a number of templates, designated by M, with a length L. The convolution size can be equal to a size of 1*M(L+N−1). After one or more rounds of downsampling and convolution, the learned feature vector (e.g., learned EEG feature vector) that is equal in length to the EEG feature vector can be determined.

In an implementation, a linear regression model can be used to generate the learned feature vector. In the linear regression model, to predict EEG features corresponding to ECG points N(ecg(t)) and include regression coefficients for an $i^{th}$ feature indicated by $\alpha_i^j$, the $i^{th}$ feature can be calculated by:

$$f_i(t) = \sum_{j=1}^{L} a_i^j \cdot exg(j)$$

The optimized solution of parameters $a_i^j$ and a weights vector w in the classifier can be generated by minimizing a cost function J(w):

$$J(w) = \text{Arg}_w \text{Min} L(w)$$
$$= \text{Arg}_w \text{Min}(-\frac{1}{N}\sum_{t=1}^{N}(q(t)\log(p(t)) + (1-q(t))\log(1-p(t)))) + \lambda \|EEGFeature_i(t) - f(t)\|^2)$$

In the above cost function J(w), $EEGFeature_i(t)$ is the EEG feature vector, p(t) is the predicted probability of finding an adverse physiological event (e.g., epilepsy), and q(t) is the real probability of finding the adverse physiological event.

The learned feature vector can include a combination of one or more of the ECG vector, the EEG vector, and the motion sensor vector.

For example, the learned feature vector can also be generated by using a linear regression model to predict, for example, EEG features corresponding to contemporaneous ECG features.

At operation 830, data including the learned feature vector can be classified to determine the plurality of time intervals that are associated with an adverse physiological event. The classifying can be based at least in part on a learning model including at least one of a support vector machine, a multilayer perceptron, and a random decision forest. The predetermined classifier discussed in operation 540 in FIG. 5A, can be further based on the classification of the learned feature vector.

Figure 8B:
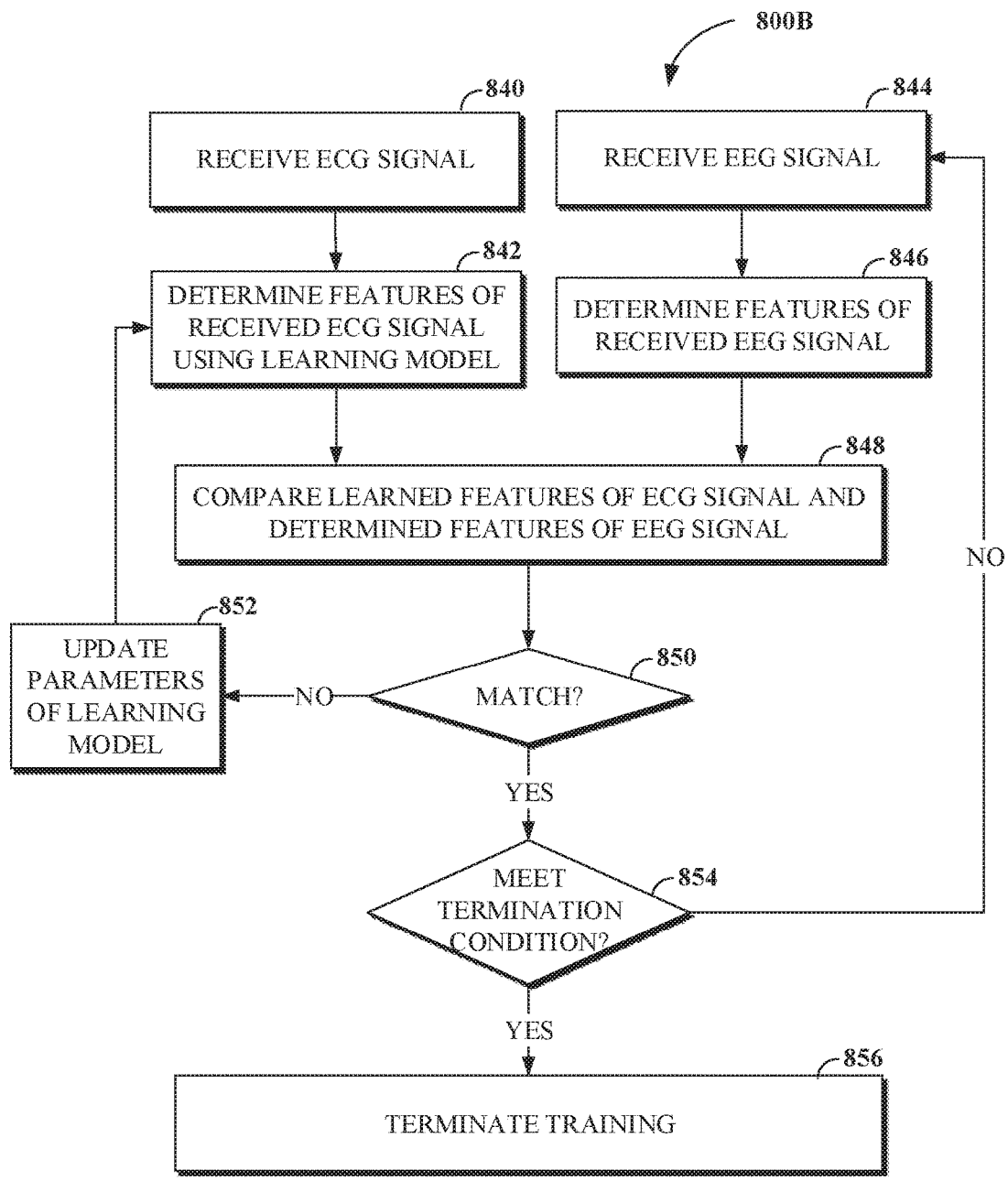
FIG. 8B is a flow diagram showing an implementation of a method for training a learning model for detecting an adverse physiological event according to implementations of this disclosure.

FIG. 8B is a flow diagram of an example process 800B for training a learning model for detection of adverse physiological events according to implementations of this disclosure. The process 800B is used to optimize parameters in the learning model, such as to maximize prediction sensitivity and/or specificity, so that EEG features can be accurately reconstructed from an ECG signal inputted to the learning model. Implementations of the process 800B which can be performed by an apparatus such as the wearable apparatus 200 shown in FIG. 2 or the computing device 300 in FIG. 3. In a further implementation, the process 800B can be performed offline (e.g., an offline learning network) by one or more computing devices.

At operation 840, an ECG signal is received. This operation is similar to the operation 810 in FIG. 8A.

At operation 842, learned feature data of the received ECG signal is determined using a learning model. The learning model can use the ECG signal (e.g., pre-processed or not pre-processed) as input to regularize the process 800B. Various learning models can be used, and structures thereof can be decided based on performance.

In some implementations, the learning model can be a CNN model. Generally, a CNN is a type of artificial neural network that includes an input layer, an output layer, and one or more middle layers in between. The middle layers can be at least one of the following layers: a convolutional layer that performs convolution on a set of learnable filters (kernels) and receptive fields of an input volume of a preceding layer, a pooling layer that performs linear or non-linear down-sampling to reduce amount of parameters to compute, a rectified linear unit (ReLU) layer that applies an activation function to boost computation speed, a fully connected layer for high-level "reasoning" (e.g., computing classification scores), and a loss layer that applies a loss function (cost function) to determine CNN prediction errors. For simplicity, further details of the framework and function of CNN components are not set forth herein.

In some implementations, the learning model can be a linear regression model. In the linear regression model, to predict EEG features corresponding to N ECG points (ecg (t)), assuming regression coefficients for an $i^{th}$ feature is indicated by $a_i^j$, the $i^{th}$ feature can be the $f_i(t)$ as described in operation 820.

At operation 844, an EEG signal is received. This operation is similar to the operation 810 in FIG. 8A. A known adverse physiological event (e.g., an epilepsy event) associated with the EEG signal can be used as a "ground truth label" for supervised learning (e.g., the CNN model) in process 800B. The process 800B can use one or more EEG signals associated with one or more known adverse physiological events.

At operation 846, feature data of the received EEG signal is determined. Determining the feature data of the EEG signal can include minimization of the EEG feature data, such as noise or interference reduction. For example, the EEG noise can include electrical activity that changes or disrupts the EEG signals. In some implementations, an EEG feature vector based on data based on EEG signals such as the aggregate EEG data can be generated.

At operation 848, the learned feature data (e.g., the ECG feature vector) and the EEG feature data (e.g., the EEG feature vector) are compared.

For example, when the learning model is the CNN model, the CNN model can convolute N ECG data points into M templates, with a length L. The convolution size can be equal to a size of 1*M(L+N−1). After one or more rounds of down-sampling and convolution, a learned feature vector (e.g., the learned EEG feature vector) that is equal in length to the EEG feature vector can be determined. For example, the learned feature vector can be generated based on a distance, such as an Euclidean distance (e.g., an $L^2$ distance), between the EEG feature vector and the ECG feature vector. In some implementations, the distance (e.g., the $L^2$ distance) between the EEG feature vector and the ECG feature vector can be used as a regularization term in the cost function of the CNN to determine the learned feature vector. In some implementations, the learned feature vector can include a combination of one or more of the ECG vector and the EEG vector.

For example, when the learning model is the linear regression model, the linear regression model can be used to generate the learned feature vector to predict, for example, EEG feature data corresponding to contemporaneous ECG feature data. The optimized solution of parameters $a_i^j$ and a weights vector w in the linear regression model can be generated by minimizing a cost function J(w) as described in operation 820 in FIG. 8A.

At operation 850, it is determined whether comparison between the learned feature data and the EEG feature data meets an accuracy condition. For example, a similarity value (e.g., a match score) can be determined as a result of the comparison, and the accuracy condition can be exceeding a similarity value threshold. When the accuracy condition is not met, process 800B proceeds to operation 852. When the accuracy condition is met, process 800B proceeds to operation 854.

At operation 852, learning parameters of the learning model (e.g., the CNN model or the linear regression model) are updated. The learning parameters are updated in a direction towards reducing prediction errors (e.g., increasing the match score). After the learning parameters are updated, process 800B goes back to operation 842, in which the ECG feature data can be re-determined using the learning model with the updated learning parameters.

At operation 854, it is determined whether a termination condition is met for process 800B. The termination condition can be, for example, all EEG signals have been used to train the learning model, or the accuracy condition cannot be met after a predetermined number of iteration of operations 842-852 or a predetermined times. When the termination condition is not met, process 800B goes back to operation 844 to receive a next EEG signal (e.g., an EEG signal of the same type as the last EEG signal or an EEG signal of a different type to the last EEG signal). When the termination condition is met, process 800B proceeds to operation 856.

At operation 856, the training process is terminated and ready for use in operation 521 in FIG. 5B.

Figure 9:
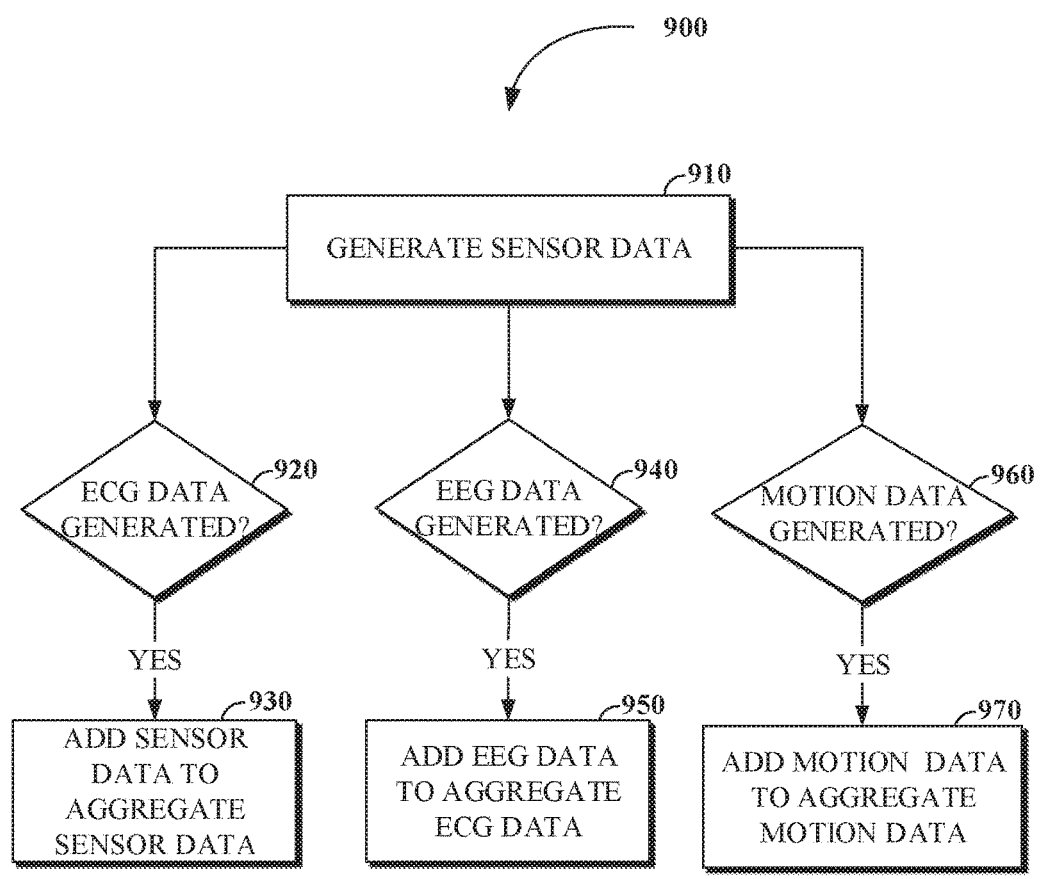
FIG. 9 is a flow diagram showing an aspect of an implementation of a method for detecting an adverse physiological event according to implementations of this disclosure.

FIG. 9 is a flow diagram of an example process 900 for detection of adverse physiological events. Implementations of the process 900 which can be performed by an apparatus such as the wearable apparatus 200 shown in FIG. 2 or the computing device 300 in FIG. 3.

At operation 910, sensor data is generated based on a sensor signal. The sensor signal can be one of the ECG signals, the EEG signals, and the motion sensor signals. The sensor data can be at least one of ECG signal data, the EEG signal data, and motion sensor signal data.

At operation 920, it is determined whether the ECG signal data is generated. Responsive to ECG signal data being generated, process 900 proceeds to operation 930. At operation 930, the ECG data is added to the aggregate ECG data. For example, ECG data generated at a wearable device can be added to locally stored aggregate ECG data or sent to a remote computing device for addition to aggregate ECG data stored on the remote computing device.

At operation 940, it is determined whether the EEG signal data is generated. Responsive to EEG signal data being generated, process 900 proceeds to operation 950. At operation 950, the ECG data is added to the aggregate ECG data. For example, ECG data generated at a wearable device can be added to locally stored aggregate ECG data or sent to a remote computing device for addition to aggregate ECG data stored on the remote computing device.

At operation 960, it is determined whether the motion signal data is generated. At operation 960, responsive to motion sensor data being generated, process 900 proceeds to operation 970. At operation 970, the motion sensor data is added to the aggregate motion sensor data. For example, motion sensor data generated at a wearable device can be added to locally stored aggregate motion sensor data or sent to a remote computing device for addition to aggregate motion sensor data stored on the remote computing device.

In some implementations, process 900 can be executed in a serial procedure. For example, operations 940-950 can be performed following operations 920-930, and followed by operations 960-970. It should be understood that, if process 900 is executed in a serial procedure, the execution order of the operations 920-930, operations 940-950, and operations 960-970 can be changed and modified to any alternative serial or parallel order or a combination thereof without any limitation.

As illustrated above, the disclosed technology can provide more effective ways to detect the occurrence of imminent adverse physiological events. The detection of adverse physiological events before the events occur can improve quality of life and safety for individuals with cardiac or neurological conditions by providing the individual or a third-party with notification that the adverse physiological event can occur.

The aspects herein can be described in terms of functional block components and various processing operations. Such functional blocks can be realized by any number of hardware and/or software components that perform the specified functions. For example, the described aspects can employ various integrated circuit components, e.g., memory elements, processing elements, logic elements, look-up tables, and the like, which can carry out a variety of functions under the control of one or more microprocessors or other control devices.

Similarly, where the elements of the described aspects are implemented using software programming or software elements the disclosure can be implemented with any programming or scripting language such as C, C++, Java, assembler, or the like, with the various algorithms being implemented with any combination of data structures, objects, processes, routines or other programming elements. Functional aspects can be implemented in algorithms that execute on one or more processors. Furthermore, the aspects of the disclosure could employ any number of techniques for electronics configuration, signal processing and/or control, data processing and the like. The words "mechanism" and "element" are used broadly and are not limited to mechanical or physical embodiments or aspects, and can include software routines in conjunction with processors and other electronic computing devices.

Implementations or portions of implementations of the above disclosure can take the form of a computer program product accessible from, for example, a computer-usable or computer-readable medium. A computer-usable or computer-readable medium can be any device that can, for example, tangibly contain, store, communicate, or transport a program or data structure for use by or in connection with any processor. The medium can be, for example, an electronic, magnetic, optical, electromagnetic, or a semiconductor device. Other suitable mediums are also available. Such computer-usable or computer-readable media can be referred to as non-transitory memory or media, and can include RAM or other volatile memory or storage devices that can change over time. A memory of an apparatus described herein, unless otherwise specified, does not have to be physically contained by the apparatus, but is one that can be accessed remotely by the apparatus, and does not have to be contiguous with other memory that might be physically contained by the apparatus.

Any of the individual or combined functions described herein as being performed as examples of the disclosure can be implemented using machine readable instructions in the form of code for operation of any or any combination of the aforementioned computational hardware. Computational code can be implemented in the form of one or more modules by which individual or combined functions can be performed as a computational tool, the input and output data of each module being passed to/from one or more further module during operation of the methods and systems described herein.

Information, data, and signals can be represented using a variety of different technologies and techniques. For example, any data, instructions, commands, information, signals, bits, symbols, and chips referenced herein can be represented by voltages, currents, electromagnetic waves, magnetic fields or particles, optical fields or particles, other items, or a combination of the foregoing.

While the disclosure has been described in connection with certain embodiments and implementations, it is to be understood that the disclosed technology is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

As used in this disclosure, an initial element described by a word or phrase, followed by the phrase "includes at least one of" and one or more additional elements described by one or more words or phrases (which can also include the term "and") can be construed to mean that the initial element includes any combination of the one or more additional elements. For example, the statement "X includes at least one of A and B" can mean: the initial element X can include the additional element A; the initial element X can include the additional element B; or that the initial element X can include both of the additional element A and the additional element B.

It is to be understood that the present disclosure is not to be limited to the disclosed implementations but, on the contrary, is intended to cover various modifications and equivalent arrangements included within the scope of the appended claims.

What is claimed is:

1. A method for detection of adverse physiological events using a wearable apparatus, the method comprising:
   receiving, by the wearable apparatus from a device attached to a wearer of the wearable apparatus, electrocardiogram (ECG) signals;
   receiving, by the wearable apparatus, motion signals;
   generating, by the wearable apparatus, physiological state data based on the ECG signals, the motion signals, and electroencephalogram (EEG) signals, wherein the physiological state data comprises EEG reconstruction data indicative of correlations between the EEG signals and at least one of the ECG signals and the motion signals, and the EEG reconstruction data is generated using at least one of the ECG signals and the motion signals,
      the ECG signals including at least one of heart rate data, PQRST cycle data, or stroke volume data;
   responsive to a plurality of features extracted from the EEG reconstruction data corresponding to at least one of a plurality of adverse physiological event profiles:
      determining, by the wearable apparatus, that an adverse physiological event is imminent; and
      alerting, the wearer of the wearable apparatus, that the adverse physiological event is imminent.

2. The method of claim 1, further comprising:
   detecting, by the wearable apparatus, at least one of ECG noise in the ECG signals and EEG noise in the EEG signals; and
   generating, by the wearable apparatus, filtered ECG signals and filtered EEG signals by respectively filtering the ECG noise from the ECG signals and the EEG noise from the EEG signals, the filtering including at least one of powerline notch filtering, bandpass filtering, wandering baseline removal, adaptive exponential filtering, and adaptive smooth filtering, wherein the physiological state data is further based on the filtered ECG signals and the filtered EEG signals.

3. The method of claim 1, wherein the motion signals include at least one of accelerometer signals and gyroscope signals, and both the motion signals and the ECG signals are used to generate the EEG reconstruction data.

4. The method of claim 1, wherein the physiological state data is further generated based on pre-processed physiological state data, the pre-processed physiological state data includes at least one of: aggregate ECG data based on a plurality of aggregate ECG signals received over a plurality of time intervals, aggregate EEG data based on a plurality of aggregate EEG signals over the plurality of time intervals, and aggregate motion data based on a plurality of aggregate motion signals over the plurality of time intervals.

5. The method of claim 4, further comprising:
   extracting, by the wearable apparatus, adverse physiological event time-domain features and adverse physiological event frequency domain features based on at least one of a first frequency and a first amplitude of the plurality of aggregate ECG signals, a second frequency and a second amplitude of the plurality of aggregate EEG signals, and a third frequency and a third amplitude of the plurality of aggregate motion signals, wherein the plurality of adverse physiological event profiles is based on at least one of the adverse physiological event time-domain features and the adverse physiological event frequency domain features.

6. The method of claim 4, further comprising:
   generating, by the wearable apparatus, at least one of an EEG feature vector based on the aggregate EEG data, an ECG feature vector based on the aggregate ECG data, and a motion feature vector based on the aggregate motion data;
   generating, by the wearable apparatus, a learned feature vector based on a distance between the EEG feature vector and the ECG feature vector or the motion feature vector; and
   classifying, by the wearable apparatus, the learned feature vector to determine the plurality of time intervals associated with the adverse physiological event, the classifying based at least in part on a learning model including at least one of a support vector machine, a multilayer perceptron, and a random decision forest, wherein the predetermined classifier is further based on the classifying the learned feature vector.

7. The method of claim 4, further comprising:
   generating, by the wearable apparatus, the EEG reconstruction data based on a comparison between the aggregate EEG data and at least one of the aggregate ECG data and the aggregate motion data, the EEG reconstruction data including correlations between the aggregate EEG data and at least one of the aggregate ECG data and the aggregate motion data, wherein the pre-processed physiological state data is based at least in part on the EEG reconstruction data.

8. The method of claim 4, further comprising:
   generating, by the wearable apparatus, at least one of ECG data and motion data, wherein the ECG data is based on at least one of the ECG signals and the motion data is based on at least one of the motion signals;
   responsive to the generating the ECG data, adding, by the wearable apparatus, the ECG data to the aggregate ECG data; and
   responsive to the generating the motion data, adding, by the wearable apparatus, the motion data to the aggregate motion data.

9. The method of claim 1,
   wherein each of the plurality of adverse physiological event profiles is associated with a respective adverse physiological event and further comprising:
      determining, by the wearable apparatus, an identity of the adverse physiological event based on the physiological state data; and
   wherein alerting, the wearer of the wearable apparatus, that the adverse physiological event is imminent comprising:
      generating, by the wearable apparatus, an alert indication including the identity of the adverse physiological event, wherein the alert indication includes at least one of a haptic alert, an audible alert, and a visual alert.

10. The method of claim 1, wherein the adverse physiological event includes at least one of a cardiovascular event, a neurological event, a central nervous system event, an ischemic event, and a hemorrhagic event.

11. An apparatus for detection of adverse physiological events, comprising:
    a sensor configured to detect motion or electrocardiogram (ECG) signals;
    a memory and a processor configured to execute instructions stored in the memory to:
       generate physiological state data based on the ECG signals and the motion signals, wherein the physiological state data comprises electroencephalogram (EEG) reconstruction data generated using at least one of the ECG signals and the motion signals;

extract a plurality of features from the physiological state data;
classify the plurality of features based on a predetermined classifier, wherein
the predetermined classifier is trained to predict the adverse physiological events based on correlations between EEG signals, and at least one of the ECG signals and the motion signals; and
responsive to the plurality of features corresponding to at least one of a plurality of adverse physiological event profiles:
determine, that an adverse physiological event is imminent; and
alert, a wearer of the apparatus, that the adverse physiological event is imminent.

12. The apparatus of claim 11, wherein the processor is further configured to execute instructions stored in the memory to:
detect at least one of ECG noise in the ECG signals and EEG noise in the EEG signals; and
generate filtered ECG signals and filtered EEG signals by respectively filtering the ECG noise from the ECG signals and the EEG noise from the EEG signals, the filtering including at least one of powerline notch filtering, bandpass filtering, wandering baseline removal, adaptive exponential filtering, and adaptive smooth filtering, wherein the physiological state data is further based on the filtered ECG signals and the filtered EEG signals.

13. The apparatus of claim 11, wherein the motion signals include at least one of accelerometer signals and gyroscope signals, and both the motion signals and the ECG signals are used to generate the EEG reconstruction data.

14. The apparatus of claim 11, wherein the physiological state data is further generated based on pre-processed physiological state data that includes at least one of: aggregate ECG data based on a plurality of aggregate ECG signals received over a plurality of time intervals, aggregate EEG data based on a plurality of aggregate EEG signals over the plurality of the time intervals, and aggregate motion data based on a plurality of aggregate motion signals over the plurality of the time intervals.

15. The apparatus of claim 14, wherein the instructions to extract the plurality of features from the physiological state data further comprise instructions stored in the memory to:
extract adverse physiological event time-domain features and adverse physiological event frequency domain features based on at least one of a first frequency and a first amplitude of the plurality of aggregate ECG signals, a second frequency and a second amplitude of the plurality of aggregate EEG signals, and a third frequency and a third amplitude of the plurality of aggregate motion signals, wherein the plurality of adverse physiological event profiles is based on at least one of the adverse physiological event time-domain features and the adverse physiological event frequency domain features.

16. The apparatus of claim 14, wherein the processor is further configured to execute instructions stored in the memory to:
generate at least one of an EEG feature vector based on the aggregate EEG data, an ECG feature vector based on the aggregate ECG data, and a motion feature vector based on the aggregate motion data;
generate a learned feature vector based on a distance between the EEG feature vector and the ECG feature vector or the motion feature vector; and classify the aggregate EEG data, the aggregate ECG data, or the aggregate motion data to determine the plurality of time intervals associated with the adverse physiological event, the classifying based at least in part on a learning model including at least one of a support vector machine, a multilayer perceptron, and a random decision forest, wherein the predetermined classifier is further based on the classifying the learned feature vector.

17. The apparatus of claim 14, wherein the processor is further configured to execute instructions stored in the memory to:
generate the EEG reconstruction data based on a comparison between the aggregate EEG data and at least one of the aggregate ECG data and the aggregate motion data, the EEG reconstruction data including correlations between the aggregate EEG data and at least one of the aggregate ECG data and the aggregate motion data, wherein the pre-processed physiological state data is based at least in part on the EEG reconstruction data.

18. The apparatus of claim 14, wherein the processor is further configured to execute instructions stored in the memory to:
generate at least one of ECG data and motion data, wherein the ECG data is based on at least one of the ECG signals and the motion data is based on at least one of the motion signals;
responsive to the generating the ECG data, add the ECG data to the aggregate ECG data; and
responsive to the generating the motion data, add the motion data to the aggregate motion data.

19. A system for detection of adverse physiological events, comprising:
a computing device; and
a wearable apparatus comprising a sensor configured to detect electrocardiogram (ECG) signals or motion, a communication component configured to exchange signal data with the computing device, a non-transitory computer readable memory, and a processor configured to execute instructions stored in the non-transitory computer readable memory to:
generate physiological state data based on at least one of pre-processed physiological state data, ECG signals, and motion signals, wherein the pre-processed physiological state data comprises electroencephalogram (EEG) reconstruction data;
extract a plurality of features from the physiological state data;
classify the plurality of features based on a predetermined classifier, wherein the predetermined classifier is trained to predict the adverse physiological events based on the EEG reconstruction data indicative of correlations between at least one of EEG signals and at least one of the ECG signals and the motion signals; and
responsive to the plurality of features corresponding to at least one of a plurality of adverse physiological event profiles:
determine, that an adverse physiological event is imminent; and
alert a wearer of the wearable apparatus that the adverse physiological event is imminent.

20. The system of claim 19, wherein the instructions stored in the non-transitory computer readable memory executed by the processor further comprise instructions to:

detect at least one of ECG noise in the ECG signals and electroencephalogram (EEG) noise in the EEG signals; and generate filtered ECG signals and filtered EEG signals by respectively filtering the ECG noise from the ECG signals and the EEG noise from the EEG signals, the filtering including at least one of powerline notch filtering, bandpass filtering, wandering baseline removal, adaptive exponential filtering, and adaptive smooth filtering, wherein the physiological state data is further based on the filtered ECG signals and the filtered EEG signals.

* * * * *